(12) United States Patent
Hamm et al.

(10) Patent No.: US 9,645,138 B2
(45) Date of Patent: May 9, 2017

(54) METHOD TO EVALUATE THE TISSUE TARGETING OF A MOLECULE OF INTEREST

(71) Applicant: IMABIOTECH, Loos (FR)

(72) Inventors: Grégory Hamm, Lille (FR); Jonathan Stauber, Haubourdin (FR)

(73) Assignee: IMABIOTECH, Loos (FR)

( * ) Notice: Subject to any disclaimer, the term of this patent is extended or adjusted under 35 U.S.C. 154(b) by 0 days.

(21) Appl. No.: 14/769,550

(22) PCT Filed: Feb. 25, 2014

(86) PCT No.: PCT/EP2014/053654
§ 371 (c)(1),
(2) Date: Aug. 21, 2015

(87) PCT Pub. No.: WO2014/128309
PCT Pub. Date: Aug. 28, 2014

(65) Prior Publication Data
US 2015/0377862 A1 Dec. 31, 2015

(30) Foreign Application Priority Data
Feb. 25, 2013 (EP) .................................. 13305211

(51) Int. Cl.
*G01N 33/50* (2006.01)
*A61K 49/00* (2006.01)

(52) U.S. Cl.
CPC ..... *G01N 33/5035* (2013.01); *A61K 49/0008* (2013.01); *G01N 33/5082* (2013.01)

(58) Field of Classification Search
CPC . Y10T 436/24; Y10T 436/00; G01N 33/3035; G01N 33/502; G01N 33/3008; G01N 33/5005; G01N 33/505; A61K 49/0008; A61K 49/0004
USPC ...................................................... 436/173
See application file for complete search history.

(56) References Cited

U.S. PATENT DOCUMENTS

| 6,689,607 B2 * | 2/2004 | Ni ...................... C07K 14/7151 435/326 |
| 9,182,409 B2 | 11/2015 | Stauber et al. |
| 2012/0258485 A1 | 10/2012 | Stauber et al. |
| 2014/0106391 A1 | 4/2014 | Stauber et al. |
| 2016/0003836 A1 | 1/2016 | Stauber et al. |

FOREIGN PATENT DOCUMENTS

| EP | 1 580 682 | 9/2005 |
| EP | 2 163 900 | 3/2010 |
| FR | 2 973 112 | 9/2012 |
| WO | WO 2007/000669 | 1/2007 |
| WO | WO 2011/073740 | 6/2011 |
| WO | WO 2012/071559 | 5/2012 |
| WO | WO 2012/126873 A1 * | 9/2012 ............. G01N 33/68 |
| WO | WO 2012/164221 | 12/2012 |
| WO | WO 2014/125112 | 8/2014 |

OTHER PUBLICATIONS

Hamm et al, Quantitative mass spectrometry imaging of propanolol and olanzapine using tissue extinction calculation as normalization factor, Journal of Proteomics, 2012, 75, 4952-4961.*
Hamm, G. et al. "Quantitative mass spectrometry imaging of propranolol and olanzapine using tissue extinction calculation as normalization factor" *Journal of Proteomics*, Aug. 30, 2012, vol. 75, No. 16, pp. 4952-4961.
Stauber, J. "Quantitation by MS imaging: needs and challenges in pharmaceuticals" *Bioanalysis*, Sep. 2012, vol. 4, No. 17, pp. 2095-2098.
Sugiura, Y. et al. "Imaging Mass Spectrometry for Visualization of Drug and Endogenous Metabolite Distribution: Toward in Situ Pharmacometabolomes" *Journal of Neuroimmune Pharmacology*, Mar. 1, 2010, vol. 5, No. 1, pp. 31-43.
Written Opinion in International Application No. PCT/EP2014/053654, Jul. 28, 2014, pp. 1-5.
Kaletas, B. K. et al. "Sample preparation issues for tissue imaging by imaging MS" *Poteomics*, 2009, pp. 2622-2633, vol. 9.
Hare, D. etal. "Three-dimensional elemental bio-imaging of Fe, Zn, Cu, Mn and P in a 6-hydroxydopamine lesioned mouse brain" *Metallomics*, Nov. 2010, pp. 745-753, vol. 2, No. 11.
Zabet-Moghaddam, M. et al. "Qualitative and quantitative analysis of lower molecular weight compounds by ultraviolet matrix-assisted laser desorption/ionization mass spectrometry using ionic liquid matrices" *Rapid Communications in Mass Spectrometry*, 2004, pp. 141-148, vol. 18.
Becker, J. Sa. et al. "Elemental imaging mass spectrometry of thin sections of tissues and analysis of brain proteins in gels by laser ablation inductively coupled plasma mass spectrometry" *Physica Status Solidi (C)*, May 1, 2007, pp. 1775-1784, vol. 4., No. 6.
Hare, D. et al. "Quantitative elemental bio-imaging of Mn, Fe, Cu, and Zn in 6-hydroxydopamine induced Parkinsonism mouse models" *Metallomics*, Jan. 1, 2009, pp. 53-58, vol. 1, No. 1.
Drexler, D. M. et al. "Utility of imaging mass spectrometry (IMS) by matrix-assisted laser desorption ionization (MALDI) on an ion trap mass spectrometer in the analysis of drugs and metabolites in biological tissues" *Journal of Pharmacological and Toxicological Methods*, May 1, 2007, pp. 279-288, vol. 55, No. 3.

(Continued)

*Primary Examiner* — Christine T Mui
(74) *Attorney, Agent, or Firm* — Saliwanchik, Lloyd & Eisenschenk

(57) ABSTRACT

The invention relates to a method for evaluating whether a molecule of interest binds or is incorporated in at least one target tissue, comprising visualizing and comparing the distribution of the molecule of interest and of at least one control compound within the target tissue or on the target tissue surface of at least one animal that has previously received the molecule of interest and/or the control compound. Advantageously, the distribution of the molecule of interest is visualized and compared with the distribution of positive and negative compounds using mass spectrometry imaging on the surface of the target tissue.

15 Claims, 7 Drawing Sheets

(56) References Cited

OTHER PUBLICATIONS

Notari, S. et al. "Determination of anti-HIV drug concentration in human plasma by MALDI-TOF/TOF" *Journal of Chromatography B.*, Mar. 20, 2006, pp. 109-116 vol. 833, No. 1.
Written Opinion in International Application No. PCT/FR2012/051205, Aug. 6, 2012, pp. 1-8.
Lemaire, R. et al. "Tag-Mass: Specific Molecular Imaging of Transcriptome and Proteome by Mass Spectrometry Based on Photocleavable Tag" *Journal of Proteome Research*, Jun. 1, 2007, vol. 6, No. 6, pp. 2057-2067.
Stauber, J. et al. "Specific MALDI-MSI: TAG-MASS" In Mass Spectrometry Imaging: Principles and Protocols, Humana Press, Jan. 1, 2010, pp. 339-361.
Written Opinion in International Application No. PCT/EP2014/053047, Apr. 16, 2014, pp. 1-6.
Tech Tip #6 Thermoscientific, "Extinction coefficients" 2008, pp. 1-3.

* cited by examiner

METHOD TO EVALUATE THE TISSUE TARGETING OF A MOLECULE OF INTEREST

CROSS-REFERENCE TO RELATED APPLICATION

This application is the U.S. national stage application of International Patent Application No. PCT/EP2014/053654, filed Feb. 25, 2014.

FIELD OF THE INVENTION

The invention relates to a method for assessing the distribution of a molecule of interest in a target tissue. More particularly, the invention provides a method for evaluating whether a molecule of interest binds or is incorporated in at least one predetermined target tissue by comparison with at least one control compound. The method of the invention allows the evaluation of the specificity, adsorption, distribution, vectorization, and metabolism of a molecule of interest and/or its metabolites to a target tissue.

The method of the invention finds its application in all domains involving the study of the behavior of a molecule of interest in a test system, namely in one or several biological tissues. The method of the invention can be advantageously used in proteomics, lipidomics or pharmaceutical research in order to screen candidate molecules and evaluate their therapeutic or diagnostic potential.

BACKGROUND OF THE INVENTION

Developing a drug, from early candidate molecule discovery up to placing the product on the market, is a long and costly process, involving significant human and equipment investment. Notably, clinical trials which involve human tests could take several years. The aim of these trials is to ensure the efficiency of the drug, highlight potential side effects and evaluate safety concerns of the therapeutics.

Upstream of these clinical trials, the preclinical trials have great importance. It is during this preclinical development that the candidate molecule is identified, selected and validated. Preclinical development specifically uses animal trials to study the pharmacology of the candidate molecule. Particularly, the purpose of these pharmacological studies is to validate in-vitro and in-vivo the mechanism of action and measure the activity of the candidate molecule in animal disease models. Moreover, they provide an evaluation of the candidate molecule's behavior and its potential transformation in a living organism and help to establish its target organs or tissue and the toxicity doses for the model.

Clinical trial relevance is consequently related to the upstream of preclinical studies during which large numbers of molecules, interesting at first sight, are finally discarded. Preclinical studies must permit a reliable selection, from dozens of candidate molecules, of the most promising one which can be an active ingredient in a drug formulation for the treatment of a given pathology. Poor preclinical evaluation may lead to the selection of a candidate molecule that will demonstrate its inefficiency in clinical phases, causing losses in terms of time and cost.

Therefore, it is important to have reliable investigations to evaluate whether a candidate molecule acts on the right target, especially on a given tissue, does not involve side effects, and is not blocked by a biological barrier. For example, numerous molecules identified in vitro as potential active compounds for central nervous system (CNS) disease treatment are unable, during in vivo trials, to cross the blood-brain barrier and thus are totally ineffective.

Today, more than 35% of candidate molecules discarded in clinical trials have been wrongly selected in preclinical phases following incorrect evaluation of their action in the target tissue.

For that reason, there is a real need for reliable methods of candidate molecule selection to ensure its high binding specificity for a given target tissue, allowing the accurate evaluation of its pharmacokinetics within this tissue. There is also a need in the case of phytosanitary product development to have more data about potential toxicity or lack of toxicity of the product on the living organism by using a method to evaluate whether a candidate molecule binds or is incorporated in at least one target tissue.

SUMMARY OF THE INVENTION

In this context, the inventors developed a method to assess the targeting efficiency of a molecule of interest for a given tissue. The method of the invention allows validation of the ability of this molecule to cross biological barrier(s) post-administration to reach said tissue as well as assessment of the specificity of the molecule for said tissue. More generally, the method of the invention allows in vivo or ex vivo/in vitro evaluation of biological parameters of the molecule of interest, such as its absorption, vectorization and/or metabolism depending on the target tissue or chosen test system.

Thus, the method of the invention can be used to achieve a fast and reliable screening of molecules with a potential therapeutic effect and select the one that may enter in a drug formulation to treat a given disease depending on a target tissue. The method of the invention can also be applied to verify potential side effects from the molecule of interest, for example on untargeted tissue(s) where the molecule can be bound. As well, the method of the invention can be used in proteomics, for example to screen biomarkers to select reliable diagnostic molecule(s) of a given pathology.

Today, a large number of molecules have been listed and classified depending on their target tissues, their specificity or lack thereof for these tissues, etc. In the present invention, the inventors propose to use this prior knowledge to select new candidate molecules. More specifically, the method according to the invention proposes to use, as a marker, a molecule with well-known properties for the target tissue and to compare its distribution in said tissue with the distribution of the candidate molecule. Any methods allowing the in vivo, ex vivo or in vitro visualization of the distribution of a molecule within tissue can be used. Particularly, the localization of the marker and the candidate molecule can be performed on a whole animal using magnetic resonance imaging (MRI) or on tissue sections, for example, using mass spectrometry imaging (MSI).

The purpose of the invention is a method for evaluating whether a molecule of interest binds or is incorporated in at least one target tissue, comprising visualizing and comparing the distribution of the molecule of interest and of at least one control compound within the target tissue or on the target tissue surface of at least one animal that has previously received the molecule of interest and/or the control compound.

The method of the invention can be used to evaluate the distribution of all molecules measurable using imaging techniques, especially a protein, a peptide, a lipid, an antibody, a nucleic acid, an inorganic or organic compound, etc. More specifically, the molecule of interest is a candidate molecule, consequently exogenous, which is involved or can be involved in a pharmaceutical or phytosanitary development. According to the invention, the candidate molecule also refers to a molecule with a pharmaceutical or phytosanitary potential or one of its metabolites.

The target tissue studied can be a whole organ, a specific region within an organ, a biological barrier, etc. For example, the target tissue is an organ such as a lung, an eye, a liver, a kidney, a heart, etc., or a biological barrier such as the blood-brain barrier, or a specific region of an organ, such as a tumor tissue, especially a cerebral tumor tissue, etc.

According to the invention, the control compound(s) and the molecule of interest may be previously co-administrated to the animal.

Advantageously, the concentrations of the control compound(s) and the molecule of interest are adapted to the studied animal model. In some embodiments, these concentrations are identical.

The administration can be performed using an enteral or parenteral route.

In a particular embodiment, the visualization and comparison of the distribution of the molecule of interest and of the control compound are performed on the surface of at least one target tissue section obtained from a previous animal tissue sampling, or tissue removal.

When mass spectrometry imaging is used, it is possible to add a step of normalization of the signals that are associated respectively with the mass spectra of the molecule of interest and with the control compound on the surface of the target tissue section. To this end, the spectral characteristic selected as the signal for the target molecule in the sample may be weighted by an extinction coefficient (TEC) specific to both the molecule and the target tissue. This weighting normalizes the signal and makes it dependent solely of the quantity of the molecule at the origin of the signal. Moreover, when a MALDI matrix is used, it is possible to weight the signal associated with the mass spectra of the target molecule and control compounds in said tissue to take into account the homogeneity deposition of the MALDI matrix.

Advantageously, the method of the invention is applied to a tissue from an animal wherein the molecule of interest and both a positive control compound and a negative control compound were previously administrated.

The method of the invention can also be used with a tissue sample from an animal wherein the molecule of interest and an intermediate control compound were previously administered.

Preferentially, the visualization step to obtain the distribution of the molecule of interest is achieved using an imaging technique, notably mass spectrometry imaging and especially MALDI imaging.

According to the invention, it is possible to evaluate the specificity of a molecule of interest for the target tissue by comparing the distribution of said molecule within the target tissue with the distribution of said molecule of interest in at least one other untargeted tissue.

According to the invention, it is possible to evaluate the tissue penetration ratio of the molecule of interest for the target tissue by comparing the distribution of said molecule within the target tissue with the distribution of a control compound within the same target tissue.

The method of the invention also allows the calculation of a tissue targeting coefficient of the molecule of interest for the targeting tissue that takes into account the specificity of the molecule for said tissue and the tissue penetration ratio of said molecule in said tissue.

In a particular embodiment, the method of the invention can comprise a step of evaluation of kinetics elimination of the molecule of interest in the target tissue that compares the distribution of said molecule in at least two sections of the target tissue that were previously obtained by sampling, at different times (t1) and (t2), from animals that were previously administered with the molecule of interest and the control compound.

The invention also concerns a computer-readable data medium comprising computer-executable instructions suited to enable a computer system to execute the comparison of the molecule of interest's distribution with one control compound's distribution according to the inventive method.

DETAILED DESCRIPTION OF THE INVENTION

Figure 1:
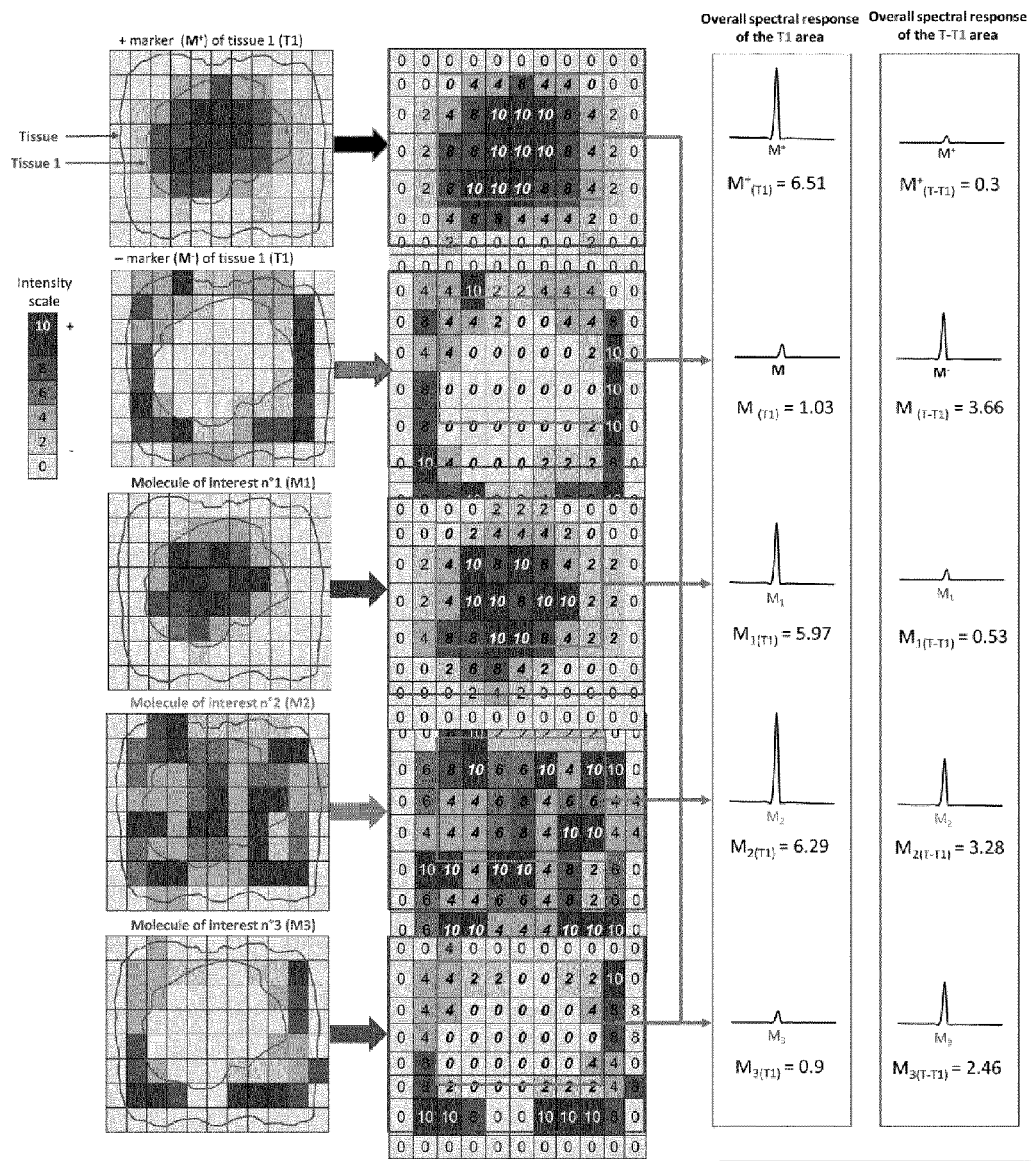
FIG. 1: Schematic representation of the distribution of three molecules of interest, M1, M2 and M3, and two control compounds, positive M+ and negative M−, obtained during a mass spectrometry imaging experiment on tissue sections comprising the target tissue (T1) and a peripheral tissue, non-targeted. The specificity of each molecule of interest is assessed by comparing the distribution (spectral signature) of the molecule of interest with the distribution (spectral signature) of the positive (M+) and negative (M−) control compounds in said target and non-target tissues.

The method of the invention is based on the comparison of the behavior in a specific target tissue of a control compound which has already-known compartmental properties for said tissue, with a molecule of interest which has unknown compartmental properties for said tissue and that has to be studied. After administration of these molecules to an animal and by comparing the distribution of these molecules in the animal's target tissue, it is possible to validate the significance or non-significance of the presence of the molecule of interest within said tissue, as well as its tissue targeting specificity, tissue penetration ratio, the relative or absolute amount in said tissue, metabolism, regulation, etc.

Depending on the molecule of interest and the target tissue, it is also possible to evaluate the best route of administration, to verify the good vectorization of the molecule in the organism or to validate its ability to cross through biological barriers to reach the target tissue.

Choice of Control Compounds

Upstream to the study of biological parameters of the molecule of interest, it is important to choose with high precision the control compounds with predetermined specificity for a target tissue that will serve as references.

A control compound is a molecule whose properties to a target tissue, i.e., its biodisponibility (ability to target a tissue), its vectorization (presence/concentration in the target tissue/ability to cross biological barriers) and/or its regulation (behavior of the molecule inside the target tissue), are already known. The control compound is usually a compound exogenous from the target tissue studied. Thus, a "positive control compound" is a molecule known to be specifically distributed in the target tissue after administration to the animal chosen as the study model. Preferentially, in order to help further data explanation, a positive control compound is not localized/distributed in the non-target tissues adjacent to the target tissue. Conversely, a "negative control compound" is a molecule known to be missing from the target tissue post-injection to the animal. According to the invention, it is also possible to use an "intermediary" control compound highlighting intermediary properties for the target tissue, compared to positive and negative control compounds. Notably, an intermediary control compound can be a molecule targeting two different tissues with the same or changed ratio (for example 60/40, 70/30, etc.). Hereinafter, "control molecule", "control" or "marker" can be used indifferently to designate a "control compound".

The choice of the control compounds is related to the target tissue studied using the method of the invention. For example, diazepam is known to be localized in the brain after injection, whereas its distribution is highly limited in the kidney. This molecule can consequently be used as a positive control compound for the brain as well as a negative control compound for the kidney. Similarly, olanzapine is localized in the brain but not in the lung. Olanzapine can consequently be used as a positive control compound for the brain as well as a negative control compound for the lung.

The molecule properties can also be dependent on the animal model studied. Thus, for a given study, the properties of the molecule of interest and control compounds are preferably always taken into account for the target tissue of the same animal model.

Advantageously, for the study of a given molecule of interest for a given target tissue, at least one positive control compound and one negative control compound are used to compare the distribution of the molecule of interest to the distribution of these two control compounds. Naturally, it also is possible to use only one control compound. In this case, a positive control compound is preferred.

To help further understand the molecules' distribution in the target tissue, control molecules which can be easily differentiated from the molecule of interest are advantageously used. For example, in the case of a mass spectrometry imaging study, control compounds with mass to charge ratios far away from the mass to charge ratio of the molecule of interest are advantageously chosen. As well, control compounds and the molecule of interest can be labeled before administration, for instance using different fluorescent markers.

To facilitate and optimize the choice of control molecules and to make it possible the method automation, all information available on molecules which potentially can be used as control compounds is advantageously listed in a database. This data may be derived from the literature (scientific papers, patents, etc.), from previous pharmaceutical studies, etc.

Examples of data which can be inserted in this database are listed in the table below for specific molecules and tissues.

TABLE 1

Examples of data to take into account in the choice of positive and negative control compounds depending on tissues or organs.

| Target Tissue | Controls +/− | m/z |
|---|---|---|
| Brain | +: Olanzapine | 313 |
| | −: Atenolol | 267 |
| Kidney | +: Oxaliplatin | 398 |
| | −: Diazepam | 285 |
| Liver | +: Propranolol | 260 |
| | −: Floroquinolone | 402 |
| Lung | +: Tiotropium | 432 |
| | −: Olanzapine | 313 |

+: positive control;
−: negative control;
m/z: masse to charge ratio

Administration of Control and Target Molecules:

Upon control(s) selection achieved, the control and target molecules have to be administrated to the animal used as the study model.

Depending on the desired study, the animal model can change. The skilled person knows which animal model is well adapted depending on the target tissue, molecule of interest, biological properties to evaluate, etc. For example, in the case of pre-clinical trials on a candidate molecule requiring the sacrifice of the animal, non-human mammals such as rodents (mice, rats, rabbits, hamsters, etc.) are preferentially used. Other non-human mammals can be used, especially monkeys, dogs, etc. In some cases, when the target tissues can be obtained using a simple biopsy, it could be interesting to use a human mammal as animal model. It is also possible to use other animal models such as fish or insects, for instance to study the impact of a molecule on the environment or a particular ecological medium.

According to an embodiment, after administration of the molecule of interest and control compound(s) to the non-human animal, said animal is sacrificed. According to the invention, the method is advantageously performed ex vivo and/or in vitro.

According to the invention and in general terms, all administration routes of the controls and target molecules can be used, such as the enteral route (i.e., drug administration by the digestion process of a gastrointestinal tract) or parenteral route (i.e., other route of administration than by the gastrointestinal tract). For example, the molecules can be administered by different routes such as epicutaneous, epidural, intra-arterial, intravenous, subcutaneous (with a specific localization), intra-cardiac, intra-cavernous injection, intra-cerebral, intradermal, intramuscular, intra-osseous infusion, intra-peritoneal, intra-thecal, intra-vesical, intra-vitreal, nasal, oral, rectal or intra-vaginal.

The administration route can be chosen depending on the molecule of interest, the tissue targeted by the method, etc.

The method of the invention can also permit the selection of the most adapted route of administration. Indeed, the method of the invention allows evaluation of the ability of a molecule of interest to cross a biological barrier to reach the target tissue. In this case, experiments are advantageously performed in parallel using the same conditions (i.e., same control compounds, same concentrations) with only the route of administration being changed.

According the invention, it is possible to deliver to the same animal several molecules of interest to simultaneously study the potential of these molecules.

In a particular embodiment, the molecule of interest and control compound(s) are co-administered to the animal, i.e., injected by means of the same medium including all said molecules. Thus, it is certain that the administration of all molecules to the animal took place at the same time (t0). Otherwise, it is possible to administer these molecules independently of one another, or the molecule of interest independently of the control compounds. In this case, the molecules are preferentially administrated to the animal at the same time (t0), for example thanks to multiples simultaneous injections.

In another embodiment, the control compound can be administered to an animal different from the animal that is administered with the molecule of interest. For example, it is possible to administer the positive control molecule to a first animal, the negative control compound to a second one and the molecule of interest to a third one. However, because of the biological variability between animals, these experimentations are preferably performed in parallel in order to decrease this variability.

In a specific embodiment, the same dose of the molecule of interest and of each control compound is administered to the animal. Thus, the evaluation step of the penetration ratio can be easily achieved.

In some cases, it may be interesting to administer different doses, or concentrations, depending on the molecules, to take into account their biological specificities for the animal model studied. Advantageously, the properties of the control compound(s) in the animal model are already known so that the skilled person knows if doses must be adapted. It is also possible to adapt the dose of the molecule of interest, for example, by comparison with an analog compound (with structural similarities) whose properties in said animal model have been already assessed.

Blood-Brain Barrier Study Case

The method of the invention can also be used to select candidate molecules in pharmaceutical development of drugs targeting the central nervous system as well as specific histological regions in the brain, especially tumor tissue. Indeed, such molecules must be able, after administration (for example via injection) to the patient, to cross the blood-brain barrier (BBB). This physiological barrier, mainly composed of endothelial cells lining the blood capillaries, separates the bloodstream from the cerebrospinal fluid. The BBB protects the brain from pathogenic agents, toxins and hormones circulating in the blood, but may also limit the penetration of some drugs. The evaluation of the BBB permeability to candidate molecules is a critical factor of efficiency measurement of a potential related treatment.

Advantageously, in such case, the method of the invention is performed using mass spectrometry imaging (MSI), widely used to study the central nervous system from its first development. The continuous improvement of spatial resolutions available during MSI experiment gives the access to fine histological and biological structure as the BBB can be.

The method of the invention allows a BBB model of study to be obtained using a positive control compound of BBB crossing (for example diazepam) and a negative control compound of BBB crossing (for example atenolol). These markers, after administration to the animal, are followed by MSI directly on the tissue section near blood vessels. Thus, it is possible to evaluate the target efficiency of the molecule of interest, such as an anticancer drug, for instance for the treatment of a multiform glioblastoma, by comparing the distribution of the molecule of interest (or its metabolites) with the distribution of the positive and/or negative markers in said tissue.

Adsorption Case Study: Receptor-Occupancy Example

In pharmacology, the receptor occupancy is defined by the capacity of an agonist (a small or large molecule such as a drug) to bind to a specific receptor or enzyme within biological tissue. This binding involves a functional response in the organism that leads to an efficient treatment of a pathology or disease. Different mechanisms can be used to achieve the binding, for example covalent linkage, ionic interaction, Van der Waals force, hydrogen binding, etc. The affinity of an agonist to a receptor can be evaluated in order to choose the best drug candidate for said receptor, exhibiting for instance a high degree of binding and full efficacy of action. A competitive binding can occur that involves for instance an agonist and an antagonist which have different affinities to the same receptor. In this case there is a competition between the two different molecules because the receptor can be bound to only one molecule at a time.

Advantageously, the method of the invention can be used to assess this competition directly within tissue sections, using MSI or any molecular imaging technique in order to evaluate the affinity of a molecule of interest (the agonist) to a specific receptor or enzyme by comparison with a positive marker (the antagonist) with a high binding affinity.

According to an embodiment, after the administration of the molecule of interest to the biological model, and sampling, the target tissue can be washed using a solution containing the antagonist (the positive marker) and allowed to incubate. Alternatively, the experiment can be performed using a co-administration of the molecules (agonist and antagonist). The positive marker (the competitive antagonist) will compete with the molecule of interest (agonist) which is already bound to the receptor. Then it is possible, using MSI, to follow the agonist and the antagonist on the dosed tissue section. The efficiency of the candidate can be evaluated by comparing the intensity and localization of the two competitive molecules on the resulting molecular images. Different parameters can be monitored, such as the agonist/antagonist concentrations, the incubation time, etc. The localization of the receptor itself on the tissue section can be assessed, depending on its ionization potential, especially for high molecular species. Different strategies can be applied to detect the receptor or enzymes on tissue (e.g., digestion, labeling, Tag-Mass). For instance, different strategies can be applied to assess receptor occupancy, by combining in/ex vivo protocols. For example, it is possible to incubate the agonist and the antagonist on the tissue section as well as to administer both compounds at the same time, etc. There is no limitation for performing these kinds of evaluation using molecular imaging.

Adduct Ion Forms

For mass spectrometry imaging experiments, all markers or target molecules can be detected as protonated $[M+H]^+$ or deprotonated $[M-H]^-$ for positive or negative ionization modes, respectively. Nevertheless, they can be detected on the mass spectrum as an adduct form with different counter ions. For example, it might be potassium $[M+K]^+$, sodium $[M+Na]^+$, chloride $[M+Cl]^-$, etc. This list is not exhaustive.

Target Tissue Preparation

The method of the invention allows visualization of a molecule of interest in at least one given target tissue of interest.

In the context of the invention, the term "tissue" refers to a set of functional grouped cells. The target tissue can be a set of similar cells with the same origin, an organ, a part of an organ, or a specific region of an organ with, optionally, multi-cell assemblies. For example, the target tissue can be a tumor localized within an organ.

According to the visualization technique used, it can be necessary or useful to perform prior preparation steps on said tissue.

According to the animal model and/or target tissue chosen, it is possible to perform an ex-vivo analysis, for example on a tissue section. In that case, the tissue or a tissue sample is sampled at a given time post-administration (t1). The sampling can be a simple biopsy, especially when the animal is a human mammal. In the case of a non-human animal, the sacrifice of the animal can be performed before sampling.

It is also possible in some cases to perform in-vivo analysis on the living whole animal.

In a particular embodiment, the analysis can be achieved on a tissue section. In this case, the tissue section can be obtained from fresh tissue, frozen tissue, or fixed/embedded tissue, for example with paraffin. All means suitable for obtaining thin tissue sections, such as a few micrometers thick, can be used.

If necessary, the tissue sections can receive a pretreatment, especially depending on the molecules to be detected, the analytical technique, etc. Thus, it is possible to use chemical or biochemical agents on tissue sections to optimize the detection of the molecule of interest and control compounds. For example, it is possible to use solvents and/or detergents to permit the detection of defined classes of molecule or improve the direct extraction of molecules from tissue. As well, it is possible to use specific enzymes capable of cleaving peptides or proteins, in order to target, for example, digested fragments which have the same localization and/or amount on the tissue as the parent molecule. It is also possible to perform antibody labeling (coupled with a tag or not), on tissue sections, or to use fluorescence-labeled molecules or radioactivity to allow the detection of the molecule of interest and control compounds.

It is also possible to change the animal model used and/or the target tissue and/or the tissue section in order to modify their abilities to bind or incorporate the molecule of interest. Thus, this treatment can include a chemical or biological modification of the animal model and/or target tissue and/or tissue section which permits the increase or inhibition of the penetration or targeting ability of a molecule of interest for a given target tissue. This treatment can be performed previously, subsequently or simultaneously to the administration of the molecule of interest and/or control compound. For example, in the case of the BBB, there are some efflux transporters in the barrier which are able to eject the molecules crossing the BBB. The effect of these transporters can be modulated (decreased or suppressed) using inhibitors or genetic modification, as a "knock-out", on the gene or the gene expression of said transporters.

If mass spectrometry imaging requiring a matrix is used to study tissue sections, notably MALDI or ME-SIMS (Matrix Enhanced Secondary Ion Mass Spectrometry), said matrix is advantageously adapted to the molecule of interest. For instance, the choice can take into account the mass range covered. The skilled person knows, from existing liquid or solid matrices, which one can be used depending on the studied molecules and/or target tissue. Similarly, all deposition methods of the matrix can be used, especially manual spraying, automatic spraying, sublimation, sieving and microspotting.

Visualization of Molecular Distribution and Generated Data Treatment

The step of distribution visualization of the molecules of interest and control compounds can be performed using any techniques allowing the accurate identification and visualization, in vivo or ex vivo, of molecules within a tissue.

Notably, in the case of in vivo analysis, it is possible to use a tomographic technique such as magnetic resonance imaging (MRI), autoradiography, positron emission tomography (PET), mono-photon emission tomography, etc.

In the case of the analysis of a tissue section, it is possible to use mass spectrometry imaging-related techniques such as MALDI imaging (Matrix-Assisted Laser Desorption/Ionization), LDI (Laser Desorption/Ionization), DESI (Desorption by Electrospray), LESA (Liquid Extraction Surface Analysis), LAESI (Laser Ablation Electrospray Ionization), DART (Direct Analysis in Real Time), SIMS (Secondary Ion Mass Spectrometry) or JEDI (Jet Desorption Electrospray Ionization), in combination with different kinds of mass analyzer as TOF (Time of Flight), Orbitrap, FTICR (Fourier Transform Ion Cyclotron Resonance), quadruple (simple or triple), etc.

It is also possible to use fluorescence, immunohistostaining or chemistry, etc. As a general rule, all techniques allowing the visualization of molecules on the surface of a tissue section can be used.

In the case of a mass spectrometry analysis, several detection modes can be used, such as direct mass spectrometry (MS) or tandem mass spectrometry (e.g., Msn, MRM, SRM). Experimental parameters such as mass range and laser fluency are fixed to optimize target detection in terms of intensity, sensitivity and resolution. Thus, the acquisition of mass spectra is performed to obtain a signal. From the mass spectra, it is possible to have access to useful data for target molecule study. For data treatment, different spectral characteristics can be used, such as the peak intensity on mass spectrum, the signal to noise ratio (S/N), the peak area, etc. Of course, for a given study, the same spectral characteristics are used to analyze the distribution of the molecule of interest and control compounds.

Results can be obtained from the same tissue section or from different sections of said tissue. In some cases, it may be preferable to use as many tissue sections as molecules studied.

According to the invention, the distribution of the molecule of interest is directly visualized on the target tissue surface, or inside the tissue during a whole-animal or whole-organ analysis. To validate these results, the distribution of the molecule of interest is compared with positive and/or negative control compound distribution. Thus, one avoids taking into consideration non-significant results.

By comparing the distribution of the molecule of interest in a target tissue with another non-target tissue, for example an adjacent tissue, it is possible to confirm whether the molecule is specifically distributed in said target tissue rather than the adjacent tissue. For instance, if the molecule is distributed both in the target tissue and the adjacent tissue, this molecule is not a good candidate for a treatment targeting specifically/exclusively said target tissue.

By comparing the distribution of the molecule of interest in the target tissue with another non-target tissue, and/or the distribution of the molecule of interest with the distribution of the positive control, it is possible to evaluate the penetration ratio or the relative amount of the molecule of interest in the target tissue. The biodisponibility of the molecule of interest, especially the proportion of said molecule reaching the target tissue compared to the administered dose, can also be assessed in an accurate way using known absolute quantification techniques.

The invention also permits a targeting coefficient for the molecule of interest to be provided for the given target tissue. This targeting coefficient takes into account the specificity of the molecule of interest for said target tissue and the penetration ratio of this molecule in the target tissue. Thus, it is possible to list the tissue targeting coefficients of several molecules, for example candidate molecules for a therapeutic treatment targeting a given tissue. These targeting coefficients might be quickly compared to select the best-adapted candidate molecule.

The method of the invention also permits the evaluation of the kinetics of elimination or the metabolism of the molecule in said tissue. For this purpose, the same molecules (interest and control) are administered at the same doses to several identical animals at the same start time (t0). The animals are then sacrificed at different times (t1 to tn). Then the distribution of the molecule of interest is compared directly on tissue sections of the target tissue sampled from each animal to have access to the scalable distribution of the molecule of interest between t0 and tn.

Normalization of the Signal

During a mass spectrometry imaging experiment, it can be important to normalize mass spectra related to each molecule to take into account the Tissue Extinction Coefficient (TEC). Additionally, a normalization step can be useful to take into consideration the matrix effect when a mass spectrometry imaging technique requiring a matrix compound is used to visualize the molecules.

More particularly, a given molecule at a given concentration does not emit a signal of the same intensity depending on the tissue in which it is detected. Similarly, two different molecules at an identical concentration in a given tissue have different signal intensities. According to the nature of the tissue and/or the localization of the molecule in said tissue, a loss or gain of intensity of the molecule's signal can be observed compared to its signal on an inert sample support or the signal of a standard molecule. This tissue extinction coefficient can be calculated for each molecule (and each target tissue), and consequently used to weight the signal obtained for each molecule.

Similarly, when the tissue section studied is covered with a matrix compound, it can induce a loss of signal intensity related to the molecule of interest. To prevent this, it is possible to calculate the extinction coefficient related to this matrix effect and use it to weight the signal obtained for each molecule studied on the analyzed tissue section.

Taking into account the TEC and/or matrix effect and corresponding normalization of signal intensity allows reliable signals to be obtained related to the real concentration of each molecule, independently of each kind of tissue and/or matrix compound used. A direct quantification of the molecules from mass spectrometry normalized results is then possible.

WO 2012/126873 relates to a method to calculate the tissue extinction coefficient and the matrix effect coefficient. It further discloses how to take into account these coefficients for the detection of a molecule within a tissue. This method can advantageously be implemented with the method of the invention to normalize the signals obtained from the molecule of interest and control compounds. Otherwise or in addition, other calculation methods allowing such normalization of mass spectra related to the studied molecule's signal can be used.

Advantageously, the normalization step of the signal is performed before the comparison of the molecules' distributions.

Mass Spectrometry Imaging Analysis

The method of the invention can be easily implemented with mass spectrometry imaging experiments. In this case, the peak intensity, peak area or signal to noise ratio of each molecule of interest and control compound are visualized and compared.

The implementation of the analysis step of the distribution of the molecule of interest according to the invention is illustrated below, in general terms, based on the use of MSI on a tissue section that comprises the target tissue and an adjacent non-target tissue surrounding said tissue. Spectral characteristics, especially peak intensities of three molecules of interest (M1, M2 and M3) as well as one positive control compound (M+) and one negative control compound (M−), are studied.

a) Distribution Analysis of the Molecule of Interest within the Target Tissue

FIG. 1 schematically shows the intensities obtained using mass spectrometry imaging of the target tissue for the three molecules of interest (M1, M2 and M3) and the control molecules (M+ and M−). These intensities reflect their distribution within the tissue.

From the spectral data directly visualized on the tissue sections, it is possible to confirm the presence or absence of each molecule of interest within the target tissue. Moreover, by comparing the spectral characteristics of the molecules of interest and control compounds, it is easy to confirm whether this distribution is significant or not.

To simplify the results, the different tissue areas are defined as two concentric squares, the target tissue corresponding to the center square (second picture column in FIG. 1). The values indicated in the small squares in the picture correspond to the normalized intensity values of each molecule. The mean of these normalized values is calculated for each molecule, for the target tissue (global spectral signature of region T1) and for the adjacent tissue (global spectral signature of region T-T1).

To evaluate the action efficiency of the molecule of interest on the target tissue, its action is weighted by taking into account its presence or absence in the non-target tissue section, i.e., the adjacent tissue noted T. For this, one links the mean intensities of the molecule of interest in and outside the target tissue to the mean intensities of the positive and negative control compounds in the same tissues.

As illustrated in FIG. 1, the M2 molecule highlights a high intensity on the whole tissue (target and non-target tissue) and is globally unspecific to target tissue T1. Conversely, the M1 molecule exhibits a high intensity in the target tissue T1 only and is almost non-detected in the adjacent tissue T. Its distribution is rather similar to the M+ molecule.

Thus, one can evaluate a first factor F1 representative of the specificity of the molecule of interest's distribution in the target tissue, using as reference values the normalized intensities of the peaks on the mass spectra of each molecule of interest, in and outside the target tissue, which are compared with the normalized intensities of the peaks of the positive and negative control compounds in and outside the target tissue. To simplify the calculation, the factor F1 of the positive control compound is considered as 100%, and the factor F1 of the negative control compound is 0%.

Table 2 below lists the intensity results obtained for each molecule.

TABLE 2

Summary of mean intensity values per molecules and tissue area
Mean intensities

|    | T1   | T – T1 | F1 (%) |
|----|------|--------|--------|
| M+ | 6.51 | 0.3    | 100%   |
| M– | 1.03 | 3.66   | 0%     |
| M1 | 5.97 | 0.53   | 90%    |
| M2 | 6.29 | 3.28   | 61%    |
| M3 | 0.90 | 2.46   | 22%    |

The F1 factor allows the molecules of interest to be ranked depending on their specificity for the target tissue.

Based on this factor alone, it is already possible to sort the molecules of interest depending on their tissue targeting specificity. Thus, in the present case, the M3 molecule, with less than 25% of spectral efficiency, can be eliminated from the candidate molecules for a treatment targeting tissue T1.

b) Analysis of the Part of the Molecule of Interest in the Target Tissue

According the invention, it is also possible to evaluate the proportion of the molecule of interest reaching the target tissue relative to the administered dose, and compared to the positive control compound.

Figure 2:
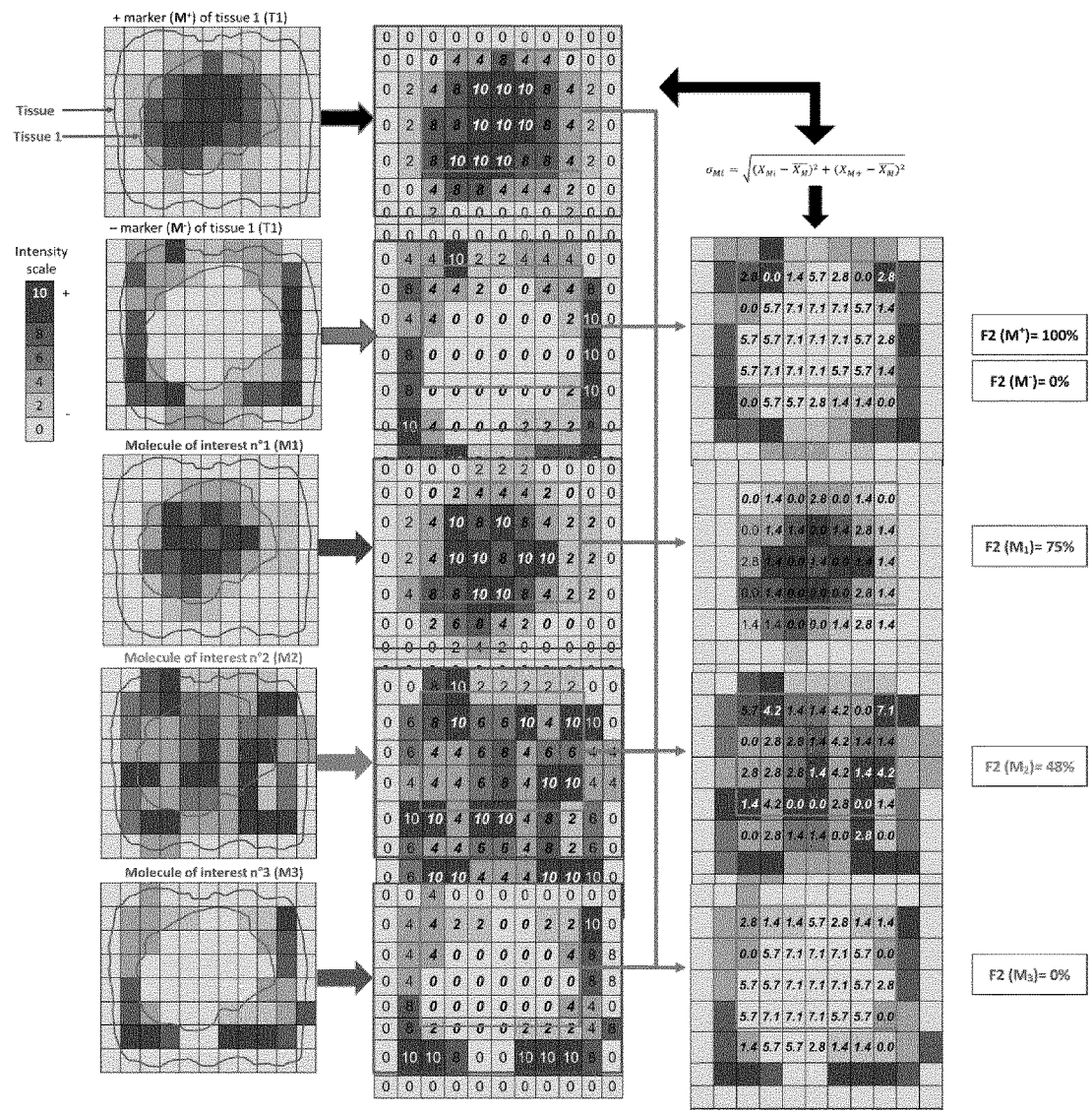
FIG. 2: Schematic representation of the distribution of the three molecules of interest, M1, M2 and M3, and the two control compounds, positive (M+) and negative (M−), obtained during mass spectrometry imaging experiment on tissue sections comprising the target tissue (T1) and a peripheral tissue, non-targeted. The similarity and/or dissimilarity of the distributions of each molecule of interest compared to the control compound distributions allows one to appreciate spatial similarities of the distribution of each molecule within the target tissue. The tissue penetration ratio for the molecules of interest is evaluated by comparing intensity maps of said molecules of interest and control compounds related to the amount of control compounds in said target tissue.

More specifically, as illustrated in FIG. 2, the method of the invention allows evaluation of the similarities and dissimilarities of the molecule of interest's distribution compared to the positive control compound in the target tissue.

Spatial similarities of the molecules' distribution are taking into account to evaluate the specific action of each one on the target tissue. For example, from the intensity map obtained for each molecule (columns 1 and 2 in FIG. 2), the standard deviation, or the variance of the molecule of interest's value, is calculated compared to the value of the positive control compound for each position (i.e., for each square having a $x_i, y_j$ position).

The standard deviation can be calculated according to the mathematical equation below:

$$\sigma_{Mi} = \sqrt{(X_{Mi} - \overline{X_M})^2 + (X_{M+} - \overline{X_M})^2}$$

$\sigma_{Mi}$: Standard deviation of the molecule of interest Mi compared to positive marker M+

$X_{Mi}$: Intensity value of the molecule of interest Mi at $(x_i, y_j)$ coordinates $X_{M+}$: Intensity value of the positive control compound M+ at $(x_i, y_j)$ coordinates $(X_M)$: Mean intensities of the molecule of interest and the positive control compound at $(x_i, y_j)$ coordinates From these standard deviation values, the method of the invention allows the calculation of a second factor, F2, highlighting the penetration ratio of the molecule of interest in the target tissue. The F2 factor corresponds to the percentage of similarity between the distribution of the molecule of interest and the positive control compound (F2=100%). Generally speaking, the F2 factor of the negative control compound is 0%. By comparing the standard deviation of the molecule of interest with the positive control compound (and eventually the negative control compound), it is possible to evaluate the F2 coefficient for said molecule of interest.

These factor F2 values obtained for each molecule of interest (M1, M2 and M3) are disclosed in FIG. 2. More specifically, this experiment shows that molecule M1 exhibits a high recovery percentage with the positive control compound M+. Regarding the molecule M2, even if M2 is detected in the target tissue area, it does not exhibit a distribution similar to the positive control compound M+. The distribution of M3 is similar to that of the negative control compound; its recovery percentage with M+ is almost zero.

c) Targeting Coefficient Calculation of a Molecule of Interest for a Given Tissue According to the invention, it is possible to calculate a targeting coefficient of a given molecule of interest for a given target tissue. This targeting coefficient reflects the specificity of said molecule for said tissue, as well as its spatial distribution (or penetration ratio) in said tissue.

For example, the targeting coefficient corresponds to the mean of the values obtained for the F1 and F2 factors for said molecule in said tissue.

Targeting coefficients (or targeting percentages) are reported in Table 3 below for each molecule of interest (M1, M2 and M3). Thus, it is possible to rank the molecules of interest depending on their action more or less efficient and more or less specific of said tissue.

TABLE 3

Summary of the targeting coefficients of the molecules of
interest and control compounds for the target tissue T1

|    | F1 (%) | F2 (%) | % Targeting |
|----|--------|--------|-------------|
| M+ | 100%   | 100%   | 100%        |
| M− | 0%     | 0%     | 0%          |
| M1 | 90%    | 75%    | 83%         |
| M2 | 61%    | 48%    | 54%         |
| M3 | 22%    | 0%     | 11%         |

In the present case, the M1 molecule is the best candidate for the target tissue T1 because it has a more targeted and specific action than the M2 molecule. The M3 molecule, as previously assessed, is not a good candidate molecule for tissue T1.

EXAMPLES

The method of the invention will now be described in further detail using specific examples and the figures presented above. These examples are given for illustrative purposes only and by no means restrict the scope of the invention. Of course, in an almost identical manner an imaging device other than MALDI can be used, such as the following: SIMS, DESI, DIOS, ICP, MALDI microscope, SNOM, SMALDI, LA-ICP, ESI (liquid extraction on tissue), MILDI, JEDI, ELDI, etc.

Example 1: Evaluation of Olanzapine Binding in Histological Regions of Kidney

In example 1, the method of the invention is used to evaluate the distribution of olanzapine in mouse kidneys and to study its targeting to specific regions of the kidney.

Material & Methods

Hydroxycinnamic acid (CHCA) from Sigma-Aldrich (Saint-Quentin-Fallavier, France)
Trifluoroacetic acid (TFA) from Sigma-Aldrich
Acetonitrile/DMSO/Water from Sigma-Aldrich
Olanzapine from Lilly Research Laboratories (Eli Lilly and Co., Indianapolis, Ind.)
Positive control compound: Posaconazole from Sigma-Aldrich
Negative control compound: Methsuximide from Sigma-Aldrich Delimitation of Target Tissue The target tissue, hereinafter "tissue 1", comprises the medulla and renal calices.

The non-target adjacent tissue, hereinafter "tissue 2", is also considered and comprises the renal cortex region.

Molecule of Interest, Positive & Negative Control Compound Selection

Olanzapine is a drug used in the treatment of certain forms of schizophrenia and bipolar disorders. It is one of the most commonly used antipsychotics. It belongs to the class of thienobenzodiazepines. Olanzapine is already known as a molecule targeting the brain. Pharmacokinetic studies have demonstrated that olanzapine was quickly absorbed by the organism and especially accumulated in the liver, spleen or kidney. Moreover, the distribution of olanzapine is highly specific to some kinds of tissue within the same organ, allowing, for the kidney example, a prominent differentiation of the cortex and medulla region. In this example, the inventors have studied the tissue targeting properties of olanzapine within the kidney.

Two positive and negative control compounds are selected for their properties to selectively target tissues 1 and 2, respectively.

Posaconazole, known to specifically bind tissue 1 and not tissue 2, is chosen as the positive control compound.

Methsuximide, known to specifically bind tissue 2 and not tissue 1, is chosen as the negative control compound.

Animal Preparation

Wild-type mice of Swiss strain weighing 25-40 g from Charles River Laboratories were used. Olanzapine, positive and negative control compounds taken up in 0.9% NaCl solution were administrated by oral route at a concentration of 8 mg/kg. Mice were sacrificed by $CO_2$ asphyxiation. Kidneys were then removed and plunged into 100% isopentane solution cooled by liquid nitrogen for rapid freezing. Finally, kidneys were stored at −80° C.

Preparation of Samples for Mass Spectrometry Imaging

Kidneys were sectioned into 10 μm thick layers (sagittal sections) using a Microm HM560 (Thermo Scientific, France) cooled at −21° C. The sections were then deposited on conductive ITO (indium tin oxide) slides (Delta Technology, USA). Finally, the sections were kept in the cryostat chamber 30 min for cryodrying and then placed in a desiccator for 30 minutes.

A CHCA matrix was used for the analysis of all kidney tissue sections. This matrix was prepared at a concentration of 10 mg/ml in acetonitrile/water+0.1% TFA (6:1, v/v). The matrix solution was deposited using the SunCollect spraying system (SunChrom, Germany) following optimized protocol.

MALDI Image Acquisition

The images were obtained using an AutoFlex Speed MALDI-TOF mass spectrometer (Bruker Daltonics, Bremen, Germany) equipped with a Smartbeam II laser. The data was generated in positive reflectron mode. A total of 500 spectra were obtained for each spot with a 1000 Hz laser frequency and a 200×200 μm$^2$ image spatial resolution on a mass range of 100 to 1000 Da. The FlexImaging version 4.0 software was used to reconstruct the images and Quantinetix 1.6 software (ImaBiotech, Loos, France) permitted the extraction of spectral intensities of ions corresponding to each studied molecule.

Localization of the Molecule of Interest and Control Compounds

Figure 3:
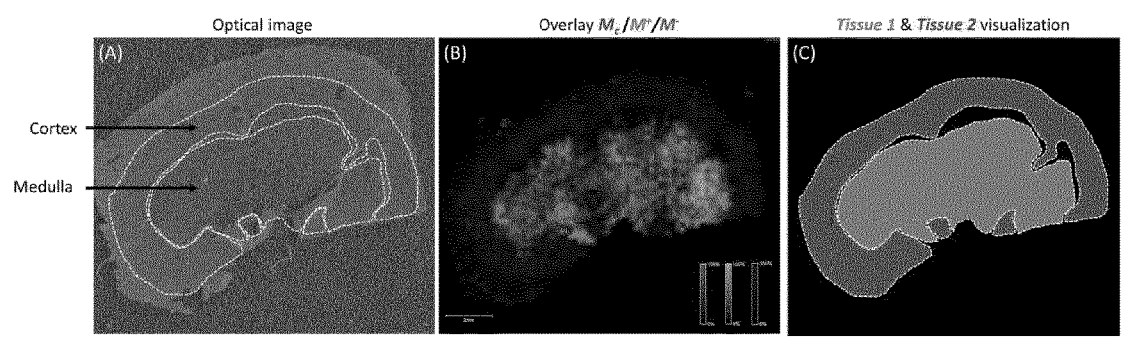
FIG. 3: Images related to histological staining (FIG. 3A), molecular distribution (FIG. 3B) and schematic view (FIG. 3C) of a mouse kidney tissue section wherein olanzapine (molecule of interest Mc), posaconazole (positive control compound M+) and methsuximide (negative control compound M−) have previously been injected. The molecular image clearly shows two different areas (FIG. 3B) respectively related to the positive control compound (center of FIG. 3B) and negative control compound (all around the positive control area of FIG. 3B). It permits one to easily delimit the target tissue, i.e., the median region of the kidney, or medulla (Tissue 1 in the center of FIG. 3C), from non-target tissue, i.e., the external region of the kidney, or renal cortex (Peripheral Tissue 2 of FIG. 3C).

Firstly, it is necessary to perform imaging mass spectrometry experiments to localize ions of interest within tissues (FIG. 3).

Images were achieved on whole kidneys. The spatial resolution used was 200 μm which permits renal sub-structures to be easily distinguished.

FIG. 3 shows a kidney tissue section, highlighting its different histological areas (FIG. 3A). The sections have been taken from the middle of the kidney.

From this, it is possible to accurately observe the target tissue. Notably, FIG. 3B shows the overlay distributions of positive and negative control compounds as well as the molecule of interest, olanzapine. It clearly shows the distinction between tissue 1 (center area of the tissue section) and tissue 2 (peripheral area of the tissue section) as presented in the schematic FIG. 3C.

These results allow evaluation of the efficiency of histological region targeting by the positive and negative control compounds. It is also important to highlight the molecule of interest within the tissue, as in the present case.

Figure 4:
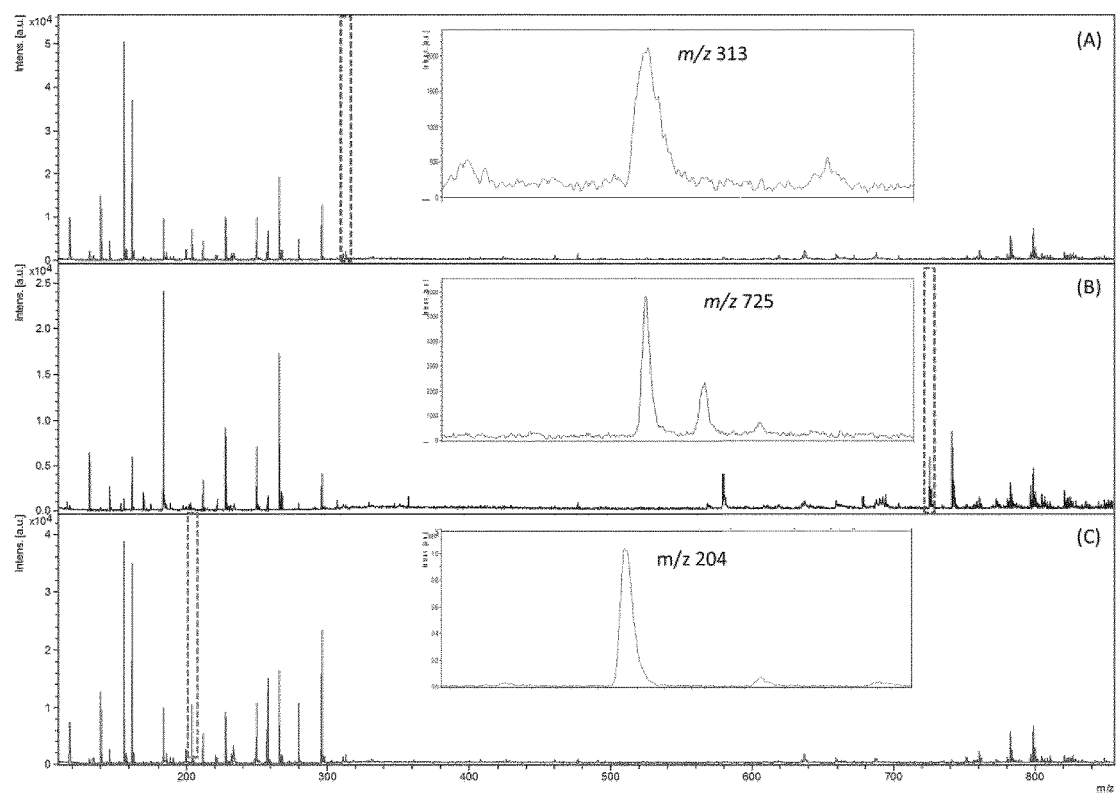
FIG. 4: Mass spectra of olanzapine (A), methsuximide (B) and posaconazole (C) corresponding respectively to discrete image coordinates at the level of high olanzapine intensity tissue area (A), non-target tissue (B) and target tissue (C). Isotopic patterns of each ion corresponding to said molecules are also presented (see inserts above each corresponding mass spectrum).

FIG. 4 displays three mass spectra corresponding to the histological areas of interest, tissue 1 for the positive control compound (m/z 204, FIG. 4C), tissue 2 for the negative control compound (m/z 725, FIG. 4B) and a high olanzapine concentrated area (m/z 313, FIG. 4A).

Results

F1 Factor Calculation

In order to calculate F1, which is related to the specificity of spatial distribution of the molecule of interest within the target tissue, one needs first to extract all intensities of the molecules of interest and control compounds from the mass spectrometric image (MS image).

Figure 5:
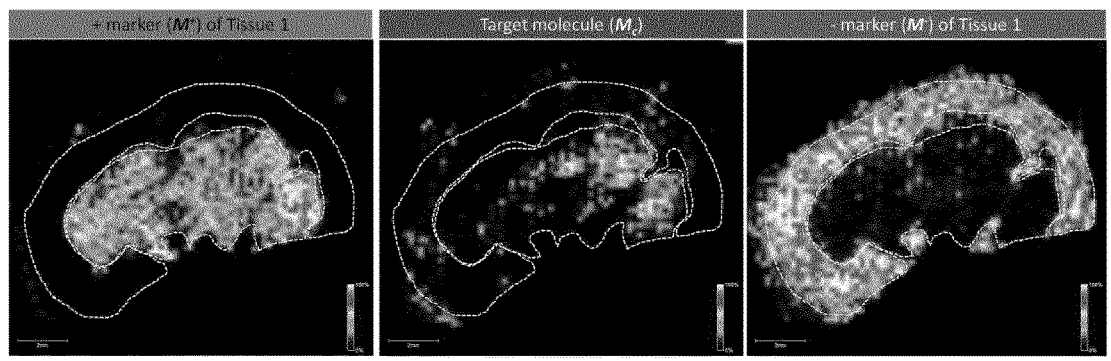
FIG. 5: Visualization on a mouse kidney tissue section of the distribution of posaconazole (positive control compound M+) at the level of the medulla region (left picture of FIG. 5), olanzapine (molecule of interest Mc) in the whole kidney (center picture of FIG. 5), and methsuximide (negative control compound M−) at the level of the renal cortex (right picture of FIG. 5) using mass spectrometry imaging. Dashed lines indicate the peripheral and median regions of the kidney.

FIG. 5 allows the distribution related to the positive and negative control compounds as well as olanzapine to be separately visualized.

Polychromatic representation gives information related to the relative intensities of the ions of interest. The maximum value of each scale is different and corresponds to the highest intensity value of each separate ion in the MS image.

Each histological region of interest is delimited on the molecular images and illustrated in FIGS. 4 and 5 with dashed lines. The imaging data treatment software Quantinetix is used to extract relative intensities of each ion of interest and control compound for each position (or voxel) within each drawn region.

The MS images in FIG. 5 illustrate:
Positive control compound (M+) distribution at the level of target tissue 1 (molecular image on the left);
Negative control compound (M−) distribution at the level of target tissue 2 (molecular image on the right); and
Olanzapine distribution at the level of target tissue T1 and non-target tissue T2 (center molecular image).

The next step is to normalize the whole dataset in order to compare them. The highest intensity related to each ion is used to normalize the intensities per position. One calculates mean normalized intensities for each ion and tissue type.

By definition, one considers that positive control compound factor F1 is equal to 100% whereas negative control compound factor F1 is equal to 0%.

The results obtained for olanzapine are reported below in Table 4.

TABLE 4

Summary of mean intensity and F1 factor values per molecules and tissue area.

| | Mean normalized intensity per tissue | | |
|---|---|---|---|
| | T1 | T2 | $F_1$ (%) |
| $M^+$ | 0.281 | 0.055 | 100% |
| $M^-$ | 0.062 | 0.241 | 0% |
| $M_c$ | 0.161 | 0.117 | 52.2% |

T1: target tissue;
T2: non target tissue;
$M_c$: Olanzapine;
$M^+$: Posaconazole;
$M^-$: Methsuximide Olanzapine's F1 factor reflects the average efficiency of the target molecule from a spectral and intensity point of view in studied tissues T1 and T2. An F1 value of 50% describes a global equilibrium of relative concentration of olanzapine in both tissues in comparison with the positive and negative compounds.

F2 Factor Calculation

The second step of tissue targeting evaluation takes into account the spatial aspect of olanzapine distribution in the kidney compared with control compounds.

The F2 factor allows comparison of the spatial distribution of control compounds with the molecule of interest, which provides information about their similarities or dissimilarities at the level of the target tissue.

Figure 6:
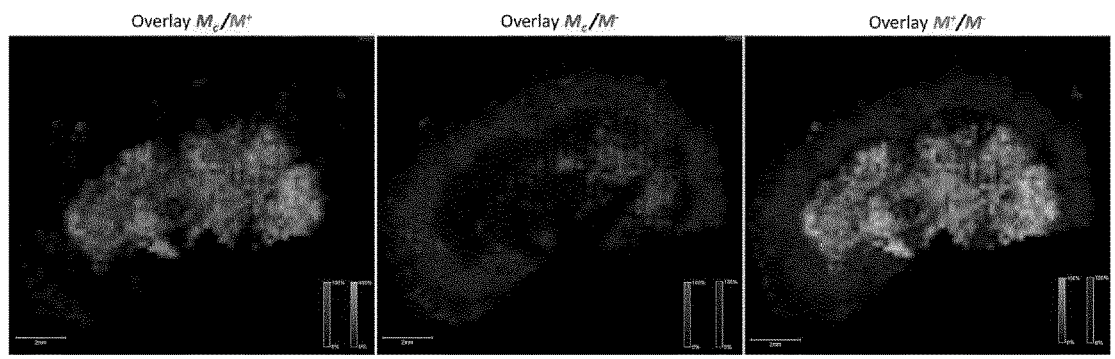
FIG. 6: Overlay of the distributions, on mouse kidney tissue section images, of the molecule of interest, Mc, and the positive control compound, M+(left picture of FIG. 6); of the molecule of interest, Mc, and the negative control compound, M− (center picture of FIG. 6); and of the two control compounds, M+ and M− (right picture of FIG. 6). The precise evaluation of similarity/dissimilarity of these distributions is easily obtained using successive overlay images.

To visualize these properties in MS images, the overlay of olanzapine and control compound distribution is shown in FIG. 6. It allows comparison of the distribution of olanzapine in the target tissue (T1) with the adjacent non-target tissue (T2).

F2 factor calculation is performed using normalized intensity values from the previous F1 factor evaluation. Position per position, one assesses the standard deviations of intensity values of the molecule of interest and the negative control with positive control one at the level of the target tissue (T1). Then the average values of standard deviation are calculated for olanzapine and the negative control compound.

By definition, the positive control compound's factor F2 is considered equal to 100% whereas the negative control compound's factor F2 is equal to 0%.

TABLE 5

Summary of F1 and F2 factors values and of global targeting coefficient (% Tg) per molecules for target tissue.

| | T1 | | |
|---|---|---|---|
| | F1(%) | F2(%) | % Tg |
| $M^+$ | 100% | 100% | 100% |
| $M^-$ | 0% | 0% | 0% |
| $M_c$ | 52.2% | 27% | 40% |

T1: target tissue;
$M_c$: Olanzapine;
$M^+$: Posaconazole;
$M^-$: Methsuximide

The F2 factor for olanzapine is evaluated at 27%, which reflects dissimilarity with the positive control distribution in target tissue. This is especially highlighted in FIG. 6 where the distribution of olanzapine is mainly localized in the right half section of the medulla (center picture of FIG. 6), whereas the positive control compound is homogenously distributed in tissue 1 (right picture of FIG. 6).

SUMMARY

Olanzapine shows a mean affinity for the medulla region. The results obtained with the method permit to conclude that olanzapine has a mean targeting behavior for one kind of tissue in the kidney instead of another, and is preferentially bound to a limited area in the medulla region.

Example 2: Adsorption Calculation

Figure 7:
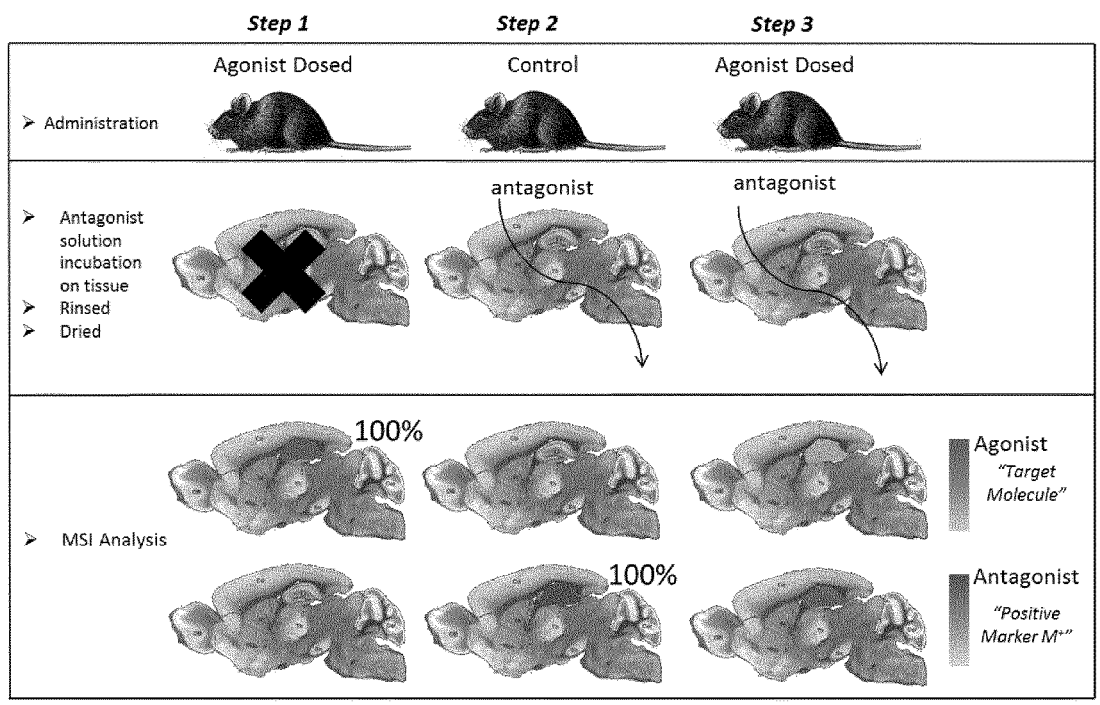
FIG. 7: Schematic representation of a strategy to assess agonists' affinity efficiency according to an embodiment of the method of the invention in the case of a receptor occupancy study.

FIG. 7 explains the methodology of adsorption of a molecule on tissue using the example of the receptor occupancy process. In this way, it is possible to measure the occupancy efficiency of the receptor by the drug (agonist) administered to the animal compared with an antagonist molecule. In this example, all the steps of the methodology are described: the dosed tissue analysis alone, the washing step with the antagonist solution of the control tissue and the combined dosed/washing analysis of the administrated sample. No negative marker is required for this kind of experiment.

In this example, the competitive binding of two benzodiazepine compounds, Diazepam (the agonist) and Lorazepam (the antagonist), which target the same receptor in the brain (GABA), are evaluated. Lorazepam has a higher affinity for this receptor, which is well established. That is why the well-known Lorazepam is used to study the affinity and efficiency of Diazepam to bind receptors in the brain. The distribution of the agonist (Diazepam) and the antagonist (Lorazepam) in the brain of a rat is studied by MALDI mass spectrometry imaging. Of course, in an almost identical manner an imaging device other that MALDI can be used, such as the following: SIMS, DESI, DIOS, ICP, MALDI microscope, SNOM, SMALDI, LA-ICP, ESI (liquid extraction on tissue), MILDI, JEDI, ELDI, etc.

Materials and Methods

Materials 2,5-Dihydroxybenzoic acid (DHB) (Sigma-Aldrich, Saint-Quentin-Fallavier, France)
Trifluoroacetic acid (TFA) (Sigma-Aldrich)
Methanol (Sigma-Aldrich)
Diazepam (LGC Standard)
Lorazepam (LGC Standard)

Animals

Wild-type rats weighing 35-40 g were used. Diazepam taken up in 0.9% NaCl solution was injected by intravenous route at a concentration of 15 mg/kg. Animals (dosed and control rats) were sacrificed by $CO_2$ asphyxiation. Brains were then removed and plunged into 100% isopentane solution cooled by liquid nitrogen for rapid freezing. Finally, brains were stored at −80° C.

Preparation of Samples for Mass Spectrometry

Brains (control and dosed tissues) were sectioned into 10 μm thick layers (coronal section) using a Microm HM560 (Thermo Scientific, France) cooled at −20° C. The sections were then deposited on conductive ITO (indium tin oxide) slides (Delta Technology, USA). Finally, the sections were kept in the cryostat chamber 15 min for cryodrying and then placed in a desiccator for 20 minutes.

Washing/Incubating Step with Antagonist Solution

The antagonist solution was prepared from a stock solution of Lorazepam at 1 mg/ml in methanol (100%). The final concentration of the washing solution was fixed at 100 pmol/μL in methanol/water+0.1% TFA (7:3). The concentration of the antagonist is a crucial factor for receptor occupancy that improves the binding capacity of the molecule. 20 μL of the solution was spotted on the tissue section (one dosed and one control sample) and then incubated for 1 hour at 37° C. in a box inside an INCU-Line incubator (VWR, France). A dosed brain section without washing was also put in the incubator.

After incubation, tissues were washed using 2 steps to remove unbound molecules from the tissue, firstly with a solution of methanol/water+0.1% TFA (7:3) corresponding to the antagonist washing solution. Secondly, the tissue is washed using only water solution (10 mL) and then placed into a desiccator for 15 min.

Preparation for Acquisition by MALDI Imaging

A DHB matrix was used for the analysis of all brain tissue sections with or without washing with the Lorazepam solution. This matrix was prepared at a concentration of 40 mg/ml in methanol/water+0.1% TFA (1:1, v/v). The matrix solution was deposited using the SunCollect spraying system (SunChrom, Germany).

MALDI Image Acquisition

The images were obtained using an AutoFlex Speed MALDI-TOF mass spectrometer (Bruker Daltonics, Bremen, Germany) equipped with a Smartbeam laser. The data was generated in positive reflectron mode. A total of 700 spectra were obtained for each spot with a 1000 Hz laser frequency and a 150×150 μm² image spatial resolution on a mass range of 0 to 1000 Da. The FlexImaging version 4.0 software was used to reconstruct the images.

Results

Figure 8:
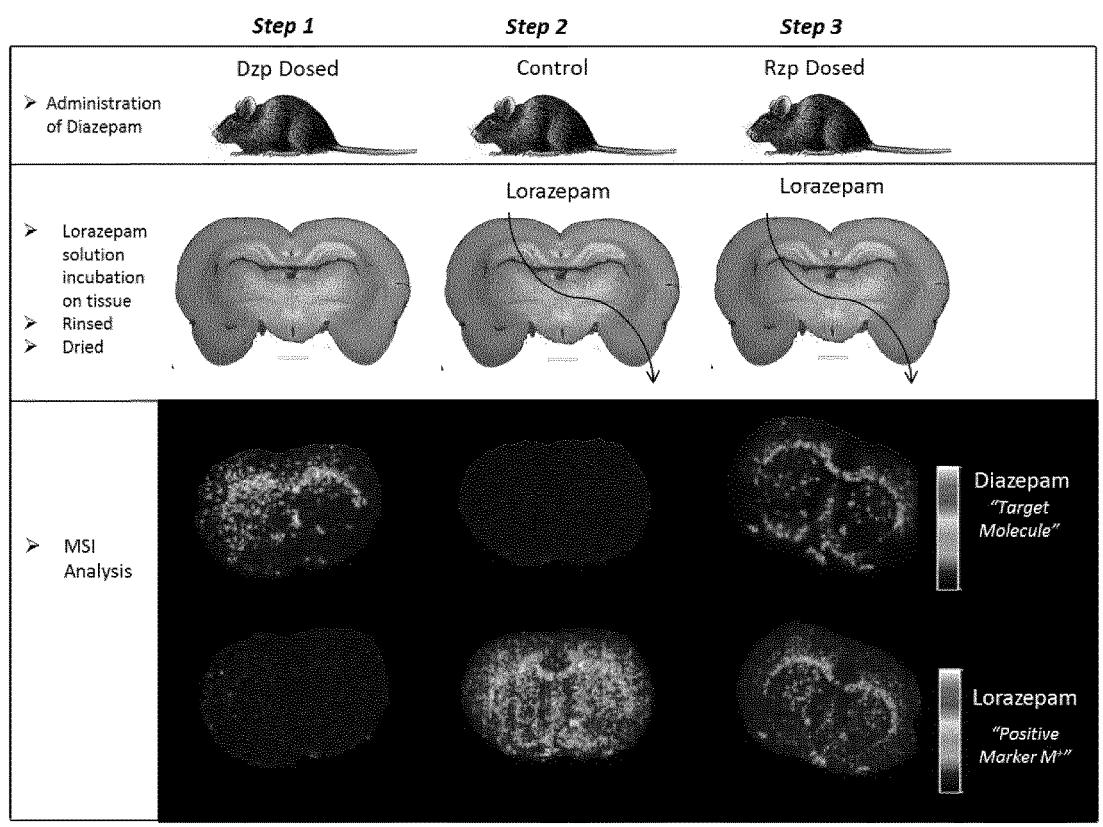
FIG. 8: Schematic representation of a strategy to assess agonists' affinity efficiency according to another embodiment of the method of the invention in the case of a receptor occupancy study.

FIG. 8 shows images obtained by MSI under different conditions by the following adsorption evaluation methodology.

The brain dosed with the agonist without washing highlights a specific localization of the Diazepam (m/z 285) at the level of the white matter of the brain. The second step involving the washing of a control tissue section with the Lorazepam solution allows observation of the Lorazepam-related ion (m/z 321) on the brain section, especially in the white matter. Obviously, no detection of Lorazepam or Diazepam was observed respectively on the dosed brain section without washing and on the control brain section with the washing step. These results give some information on the receptor binding sites of the two benzodiazepam species, i.e., the white matter. Finally, the last experiment combines the Diazepam-dosed tissue with the Lorazepam washing step. This image is further used to calculate the efficiency and the affinity of Diazepam according to Lorazepam response.

In summary, the experiment provides:

The distribution of the target molecule (Mc), Diazepam;

The distribution of the positive marker (M+), Lorazepam; and

The targeted area (T1), the white matter (receptor binding site) and the untargeted area (T2), the rest of the brain.

F1 Factor; Intensity Factor

In order to calculate the factor 1, which is related to spectral parameters of the target molecule at the level of the targeted tissue, one needs first to extract the intensity of Diazepam and Lorazepam ions in the specific area of the brain.

Then the methodology is applied to calculate F1 on the dataset.

TABLE 6

Summary of mean intensity values and corresponding F1 factor per molecule and tissue

| | Normalized mean intensity/Tissue | | |
|---|---|---|---|
| | T1 | T2 | $F_1$ (%) |
| $M^+$ | 0.821 | 0.21 | 100% |
| $M_c$ | 0.692 | 0.117 | 85.1% |

T1: Targeted Area;
T2: untargeted area;
$M_c$: Diazepam;
$M^+$: Lorazepam

F2 Factor; Spatial Factor

The second step of the affinity assessment of Diazepam takes into account its spatial distribution at the level of the targeted area versus positive marker localization. The F2 factor allows comparison of the fine localization of the agonist and the antagonist in the white matter region and gives information about their similarity or dissimilarity.

TABLE 7

Summary of F1 and F2 values and corresponding targeting coefficient (% Tar) for Diazepam on target area (Receptor) T1

|       | F1(%) | F2(%) | % Tar |
|-------|-------|-------|-------|
| $M^+$ | 100%  | 100%  | 100%  |
| $M_c$ | 85.1% | 72.5% | 78.8% |

T1: Targeted Area;
$M_c$: Diazepam;
$M^+$: Lorazepam

The F2 factor is equal to 72.5%, which showed a high similarity of the Diazepam and Lorazepam distribution in the targeted area (receptor site). Diazepam is highly localized in the white matter of the brain, as is its antagonist Lorazepam.

CONCLUSION

In conclusion, the two factors can be combined to estimate the global targeting factor of the agonist as presented in Table 7. Diazepam shows a high affinity for the receptor site of benzodiazepine regarding the positive marker studied. The targeting of Diazepam is highly efficient for the white matter region of the brain.

The invention claimed is:

1. A method for detecting a molecule of interest in at least one target tissue,
   the method comprising the steps of:
   administering the molecule of interest to at least one animal;
   selecting at least one control compound for detection, wherein the properties of the at least one control compound in binding or incorporating in the at least one target tissue are known;
   sampling at least one section of the target tissue from the at least one animal at a given time post administration of the molecule of interest; and
   detecting the distribution on the surface of the at least one target tissue section of:
   i) the molecule of interest, and
   ii) the at least one control compound.

2. The method according to claim 1, wherein the at least one control compound comprises a positive control compound and a negative control compound.

3. The method according to claim 1, wherein the molecule of interest and the at least one control compound are co-administered to the animal.

4. The method according to claim 1, wherein the same concentration of the at least one control compound and the molecule of interest are administered to the animal.

5. The method according to claim 1, wherein the molecule of interest and/or the at least one control compound are administered enterally or parenterally to the animal.

6. The method according to claim 1, wherein the detection of the distribution of the molecule of interest and the at least one control compound comprises an imaging technique.

7. The method according to claim 6, wherein the detection of the distribution of the molecule of interest and the at least one control compound comprises mass spectrometry molecular imaging.

8. The method according to claim 6, wherein signals related to the imaging technique of the molecule of interest and the at least one control compound are normalized to take into account a tissue extinction coefficient (TEC) and/or biological matrix effect.

9. The method according to claim 7, wherein signals related to mass spectra of the molecule of interest and the at least one control compound are normalized to take into account a tissue extinction coefficient (TEC) and/or biological matrix effect.

10. The method according to claim 1, wherein specificity of the molecule of interest for the target tissue comprises detecting the distribution of said molecule in the target tissue and detecting the distribution of said molecule in at least one non-target tissue.

11. The method according to claim 1, the method further comprising the steps of:
    sampling a first target tissue section of the at least one target tissue of the at least one animal, at a first given time (t1) post administration of the molecule of interest;
    sampling a second target tissue section of the at least one target tissue of the at least one animal, at a second given time (t2) post administration of the molecule of interest; and
    detecting the distribution of the molecule of interest in the target tissue sections taken at t1 and t2.

12. The method according to claim 1, wherein the molecule of interest is a candidate molecule, a therapeutic potential molecule or a phytosanitary potential molecule or one of its metabolites.

13. The method according to claim 1, wherein said at least one animal or the at least one target tissue of said animal or the tissue section of the target tissue of said animal is treated to modify its capacity to bind and/or incorporate the molecule of interest within the target tissue.

14. A computer-readable data medium comprising computer-executable instructions suited to enable a computer system to execute the comparison of the distribution of the molecule of interest with the distribution of at least one control compound according to the method of claim 1.

15. The method according to claim 1, said method comprising the administration of said at least one selected control compound to said animal.

* * * * *